US008731675B2

(12) United States Patent
Ranu et al.

(10) Patent No.: US 8,731,675 B2
(45) Date of Patent: May 20, 2014

(54) NEUROSTIMULATION SYSTEM AND METHOD FOR PROVIDING THERAPY TO PATIENT WITH MINIMAL SIDE EFFECTS

(75) Inventors: Emarit A. S. Ranu, Fort Collins, CO (US); Bradley L. Hershey, Valencia, CA (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 201 days.

(21) Appl. No.: 13/253,735

(22) Filed: Oct. 5, 2011

(65) Prior Publication Data

US 2012/0089200 A1    Apr. 12, 2012

Related U.S. Application Data

(60) Provisional application No. 61/390,327, filed on Oct. 6, 2010.

(51) Int. Cl.
*A61N 1/34* (2006.01)
(52) U.S. Cl.
USPC .......................................... 607/46
(58) Field of Classification Search
USPC ................................... 607/45–46
See application file for complete search history.

(56) References Cited

U.S. PATENT DOCUMENTS

| 6,895,280 B2 | 5/2005 | Meadows et al. |
| 2010/0125313 A1 | 5/2010 | Lee et al. |

OTHER PUBLICATIONS

De Ridder D et al, Burst spinal cord stimulation: toward paresthesia-free pain suppression, Neurosurgery. May 2010; 66(5):986-90.
DiMarco AF et al, "Mechanism of expiratory muscle activation during lower thoracic spinal cord stimulation", J Appl Physiol. Jun. 2002; 92(6):2341-6.
Tai C, et al. "Stimulation analysis of conduction block in unmyelinated axons induced by high-frequency biphasic electrical currents", IEEE Trans Biomed Eng., 52(7):1323-32, 2005.
Williamson R.P., et al., "Localized electrical nerve blocking", IEEE Trans Biomed Eng., 52(3): 362-70, 2005.

*Primary Examiner* — Amanda Patton
(74) *Attorney, Agent, or Firm* — Vista IP Law Group LLP (57) ABSTRACT

A method comprises conveying a pulsed waveform between an electrode and a stimulation site of a spinal cord, thereby evoking the antidromic propagation of action potentials along a first sensory neural fiber creating a therapeutic effect in the tissue region, evoking the orthodromic propagation of action potentials along the first sensory neural fiber potentially creating paresthesia corresponding to the tissue region, and evoking the antidromic propagation of action potentials along a second sensory neural fiber potentially creating a side-effect in another tissue region. The method further comprises conveying electrical energy between an electrode and a blocking site rostral to the stimulation site, thereby blocking the action potentials propagated along the first sensory neural fiber and reducing the paresthesia, and conveying electrical energy between an electrode and a blocking site caudal to the stimulation site, thereby blocking the action potentials propagated along the second sensory neural fiber and reducing the side-effect.

22 Claims, 4 Drawing Sheets

FIG. 4

NEUROSTIMULATION SYSTEM AND METHOD FOR PROVIDING THERAPY TO PATIENT WITH MINIMAL SIDE EFFECTS

RELATED APPLICATION DATA

The present application claims the benefit under 35 U.S.C. §119 to U.S. provisional patent application Ser. No. 61/390, 327, filed Oct. 6, 2010. The foregoing application is hereby incorporated by reference into the present application in its entirety.

FIELD OF THE INVENTION

The present invention relates to tissue stimulation systems and methods, and more particularly, to systems and methods for limiting the stimulation of nerve tissue to a specific target region.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications, such as angina pectoris and incontinence. Deep Brain Stimulation (DBS) has also been applied therapeutically for well over a decade for the treatment of refractory Parkinson's Disease, and DBS has also recently been applied in additional areas, such as essential tremor and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients. Furthermore, in recent investigations Peripheral Nerve Stimulation (PNS) systems have demonstrated efficacy in the treatment of chronic pain syndromes and incontinence, and a number of additional applications are currently under investigation. Occipital Nerve Stimulation (ONS), in which leads are implanted in the tissue over the occipital nerves, has shown promise as a treatment for various headaches, including migraine headaches, cluster headaches, and cervicogenic headaches.

Each of these implantable neurostimulation systems typically includes one or more electrode carrying stimulation leads, which are implanted at the desired stimulation site, and a neurostimulator implanted remotely from the stimulation site, but coupled either directly to the stimulation lead(s) or indirectly to the stimulation lead(s) via a lead extension. Thus, electrical pulses can be delivered from the neurostimulator to the stimulation electrode(s) to stimulate or activate a volume of tissue in accordance with a set of stimulation parameters and provide the desired efficacious therapy to the patient. In particular, electrical stimulation energy conveyed to the electrodes creates an electrical field, which when strong enough, depolarizes (or "stimulates") the neural fibers within the spinal cord beyond a threshold level, thereby inducing the firing of action potentials (APs) that propagate along the neural fibers to provide the desired efficacious therapy to the patient.

The combination of electrodes used to deliver electrical pulses to the targeted tissue constitutes an electrode combination, with the electrodes capable of being selectively programmed to act as anodes (positive), cathodes (negative), or left off (zero). In other words, an electrode combination represents the polarity being positive, negative, or zero. Other parameters that may be controlled or varied include electrical pulse parameters, which may define the pulse amplitude, pulse width, pulse rate, pulse shape, and burst rate. Each electrode combination, along with the electrical pulse parameters, can be referred to as a "stimulation parameter set."

The neurostimulation system may further comprise a handheld patient programmer to remotely instruct the neurostimulator to generate electrical stimulation pulses in accordance with selected stimulation parameters. The handheld programmer in the form of a remote control (RC) may, itself, be programmed by a clinician, for example, by using a clinician's programmer (CP), which typically includes a general purpose computer, such as a laptop, with a programming software package installed thereon.

In the context of an SCS procedure, one or more stimulation leads are introduced through the patient's back into the epidural space, such that the electrodes carried by the leads are arranged in a desired pattern and spacing to create an electrode array. One type of commercially available stimulation leads is a percutaneous lead, which comprises a cylindrical body with ring electrodes, and can be introduced into contact with the affected spinal tissue through a Touhy-like needle, which passes through the skin, between the desired vertebrae, and into the epidural space. For unilateral pain, a percutaneous lead is placed on the corresponding lateral side of the spinal cord. For bilateral pain, a percutaneous lead is placed down the midline of the spinal cord, or two or more percutaneous leads are placed down the respective sides of the midline of the spinal cord, and if a third lead is used, down the midline of the spinal cord. After proper placement of the neurostimulation leads at the target area of the spinal cord, the leads are anchored in place at a spinal site to prevent movement of the neurostimulation leads. To facilitate the location of the neurostimulator away from the exit point of the neurostimulation leads, lead extensions are sometimes used.

The neurostimulation leads, or the lead extensions, are then connected to the IPG, which can then be operated to generate electrical pulses that are delivered, through the electrodes, to the targeted tissue. It is believed that the antidromic activation of the large diameter sensory neural fibers in the spinal cord (i.e., the APs propagate in a direction opposite to their normal direction, which in the case of the sensory neural fibers in the spinal cord, propagate in the caudal direction) provides the actual pain relief to the patient by reducing/blocking transmission of smaller diameter sensory neural fibers of the spinal cord via interneuronal interaction in the dorsal horn of the spinal cord, while the orthodromic activation of the large diameter sensory neural fibers in the spinal cord (i.e., the APs propagate in their normal direction, which in the case of the sensory neural fibers in the spinal cord, propagate in the rostral direction) generate APs that arrive at the thalamus and are relayed to the sensory cortex, thereby creating a side-effect in the form of a sensation known as paresthesia, which can be characterized as an tingling sensation. Thus, the sensation of paresthesia is concordant with the pain region of the patient, and typically must be present for pain mitigation.

Stimulation energy may be delivered to the electrodes during and after the lead placement process in order to verify that the electrodes are stimulating the target neural elements and to formulate the most effective stimulation regimen (i.e., the best stimulation parameter set or sets). The stimulation regimen will typically be one that provides stimulation energy to all of the target tissue that must be stimulated in order to provide the therapeutic benefit, yet minimizes the volume of non-target tissue that is stimulated.

Intra-operatively (i.e., during the surgical procedure), the neurostimulator may be operated to test the effect of stimulation and adjust the parameters of the stimulation for optimal pain relief. The patient may provide verbal feedback regarding the presence of paresthesia over the pain area, and based on this feedback, the lead positions may be adjusted and re-anchored if necessary. A computer program, such as Bionic Navigator®, available from Boston Scientific Neuromodulation Corporation, can be incorporated in a clinician's programmer (CP) (briefly discussed above) to facilitate selection of the stimulation parameters. Any incisions are then closed to fully implant the system. Post-operatively (i.e., after the surgical procedure has been completed), a clinician can adjust the stimulation parameters using the computerized programming system to re-optimize the therapy.

While the electrical stimulation of the spinal cord has generally been successful in providing pain therapy to a patient, the side-effect of paresthesia that typically accompanies the pain therapy limits the amplitude of the electrical stimulation that can be applied to the targeted spinal cord region. That is, although an increase in the amplitude of the electrical stimulation may optimize mitigation of the pain in a targeted region of the patient, such increase in the amplitude may undesirably result in paresthesia that is too intense for the patient to tolerate. As a result, the pain experienced by the patient may not be eliminated or otherwise reduced to a sufficient level that might have otherwise occurred in the absence of the paresthesia.

Furthermore, because the target neural tissue (i.e., the tissue associated with the therapeutic effects) and non-target neural tissue (i.e., the tissue associated with undesirable side-effects) are often juxtaposed, therapeutically stimulating neural tissue while preventing side-effects as a result of stimulating non-target neural tissue may be difficult to achieve. For example, electrical stimulation of the spinal cord may evoke action potentials that ultimately lead to subsequent action potentials propagated in motor neural fibers via motor reflex spinal cord loops, which may, in turn, lead to undesirable outcomes (e.g., discomfort or involuntary movements) for the patient. Thus, inadvertent stimulation of non-target neural tissue may also limit the amplitude of the electrical stimulation that can be applied to the targeted spinal cord region.

There, thus, remains a need to stimulate targeted spinal cord tissue at an amplitude sufficient to optimize therapy for the patient without creating side-effects, such as uncomfortable paresthesia and involuntary motor movements.

SUMMARY OF THE INVENTION

In accordance with a first aspect of the present inventions, a method of providing therapy to a tissue region of a patient using first and second electrodes is provided. The method comprises conveying an electrical pulsed waveform between the first electrode and a stimulation site of a spinal cord of the patient, thereby evoking the antidromic propagation of action potentials along at least one sensory neural fiber of the spinal cord that creates a therapeutic effect (e.g., pain relief) in the tissue region, and evoking the orthodromic propagation of action potentials along the sensory neural fiber(s) that potentially creates a sensation of paresthesia in the brain of the patient corresponding to the tissue region. In one method, the action potentials antidromically propagated along the sensory neural fiber(s) reduce, via interneuronal interaction in a dorsal horn of the patient, antidromic propagation of action potentials in painful sensory neural fibers of the spinal cord innervating the tissue region.

The method further comprises conveying electrical energy between the second electrode and a blocking site of the spinal cord rostral to the stimulation site, thereby blocking the orthodromically propagated action potentials and reducing (and preferably eliminating) the paresthesia that would have otherwise been caused in the patient in the absence of the conveyed electrical energy. As one example, the electrical energy may be sinusoidal having a frequency greater than the electrical pulsed waveform (e.g., if the pulse rate of the electrical pulsed waveform is 2 Hz-1200 Hz, the frequency of the electrical energy may be greater than 1200 Hz, and preferably greater than 2000 Hz).

In an optional method, the electrical pulsed waveform between the first electrode and the stimulation site evokes the antidromic propagation of action potentials along at least another sensory neural fiber of the spinal cord that potentially creates a side-effect (e.g., involuntary motor movement) in another tissue region of the patient, in which case, the method may further comprise conveying additional electrical energy between a third electrode and a blocking site of the spinal cord caudal to the stimulation site, thereby blocking the action potentials antidromically propagated along the at least one other sensory neural fiber and reducing the side-effect that would have otherwise been caused in the patient in the absence of the additionally conveyed electrical energy.

In accordance with a second aspect of the present inventions, another method of providing therapy to a tissue region of a patient using first and second electrodes is provided. The method comprises conveying an electrical pulsed waveform between the first electrode and a stimulation site of a spinal cord of the patient, thereby evoking the antidromic propagation of action potentials along at least a first sensory neural fiber of the spinal cord that creates a therapeutic effect (e.g., pain relief) in the tissue region, and evoking the antidromic propagation of action potentials along at least a second sensory neural fiber of the spinal cord potentially creates a side-effect in another tissue region (e.g., involuntary motor movement of the other tissue region). The first sensory neural fiber(s) terminates in the dorsal horn of the spinal cord at a first vertebral level, and the second sensory fiber(s) terminate in the dorsal horn at a second vertebral level caudal to the first vertebral level. In one method, the action potentials antidromically propagated along the first sensory neural fiber(s) reduce, via interneuronal interaction in a dorsal horn of the patient, propagation of painful action potentials in sensory neural fibers of the spinal cord innervating the tissue region.

The method further comprises conveying electrical energy between the second electrode and a blocking site of the spinal cord between the first and second vertebral levels, thereby blocking the action potentials antidromically propagated along the second neural fiber(s) and reducing (preferably, eliminating) the side-effect that would have otherwise been caused in the patient in the absence of the conveyed electrical energy. As one example, the electrical energy may be sinusoidal having a frequency greater than the electrical pulsed waveform (e.g., if the pulse rate of the electrical pulsed waveform is 2 Hz-1200 Hz, the frequency of the electrical energy may be greater than 1200 Hz, and preferably greater than 2000 Hz).

In an optional method, the electrical pulsed waveform between the first electrode and the stimulation site evokes the orthodromic propagation of action potentials along the sensory neural fiber(s) that potentially creates a sensation of paresthesia in the brain of the patient corresponding to the tissue region, in which case, the method may comprise conveying additional electrical energy between a third electrode and a blocking site of the spinal cord rostral to the stimulation site, thereby blocking the orthodromically propagated action potentials and reducing the paresthesia that would have otherwise been caused in the patient in the absence of the conveyed electrical energy.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
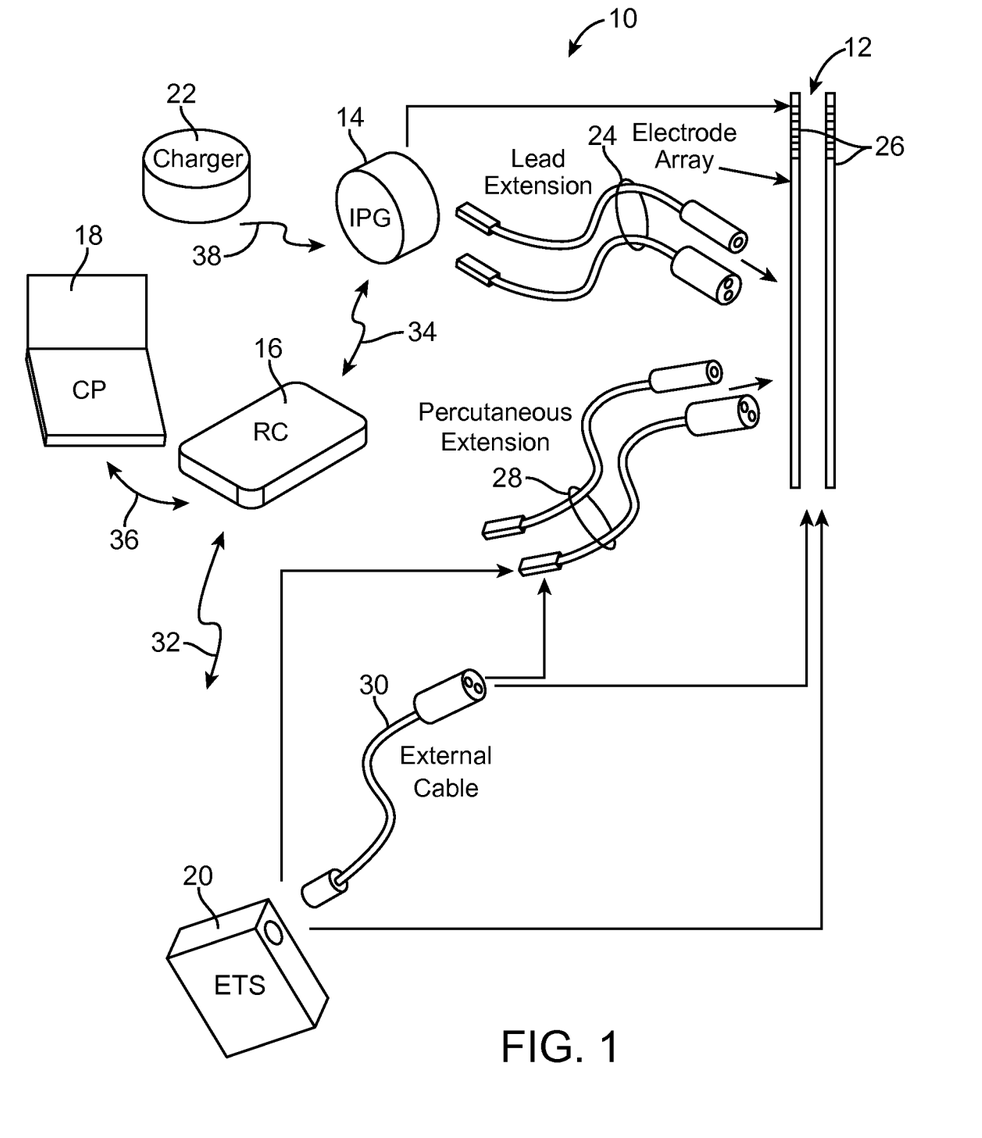
FIG. 1 is plan view of one embodiment of a spinal cord stimulation (SCS) system arranged in accordance with the present inventions.

Turning first to FIG. 1, an exemplary spinal cord stimulation (SCS) system 10 generally includes one or more (in this case, two) implantable stimulation leads 12, a pulse generating device in the form of an implantable pulse generator (IPG) 14, an external control device in the form of a remote controller RC 16, a clinician's programmer (CP) 18, an external trial stimulator (ETS) 20, and an external charger 22.

The IPG 14 is physically connected via one or more percutaneous lead extensions 24 to the stimulation leads 12, which carry a plurality of electrodes 26 arranged in an array. In the illustrated embodiment, the stimulation leads 12 are percutaneous leads, and to this end, the electrodes 26 are arranged in-line along the stimulation leads 12. In alternative embodiments, the electrodes 26 may be arranged in a two-dimensional pattern on a single paddle lead. As will be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20 may also be physically connected via the percutaneous lead extensions 28 and external cable 30 to the stimulation leads 12. The ETS 20, which has similar pulse generation circuitry as that of the IPG 14, also delivers electrical stimulation energy in the form of a pulsed electrical waveform to the electrode array 26 in accordance with a set of stimulation parameters. The major difference between the ETS 20 and the IPG 14 is that the ETS 20 is a non-implantable device that is used on a trial basis after the stimulation leads 12 have been implanted and prior to implantation of the IPG 14, to test the responsiveness of the stimulation that is to be provided. Further details of an exemplary ETS are described in U.S. Pat. No. 6,895,280, which is expressly incorporated herein by reference.

The RC 16 may be used to telemetrically control the ETS 20 via a bi-directional RF communications link 32. Once the IPG 14 and stimulation leads 12 are implanted, the RC 16 may be used to telemetrically control the IPG 14 via a bi-directional RF communications link 34. Such control allows the IPG 14 to be turned on or off and to be programmed with different stimulation parameter sets. The IPG 14 may also be operated to modify the programmed stimulation parameters to actively control the characteristics of the electrical stimulation energy output by the IPG 14.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The clinician detailed stimulation parameters provided by the CP 18 are also used to program the RC 16, so that the stimulation parameters can be subsequently modified by operation of the RC 16 in a stand-alone mode (i.e., without the assistance of the CP 18). The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
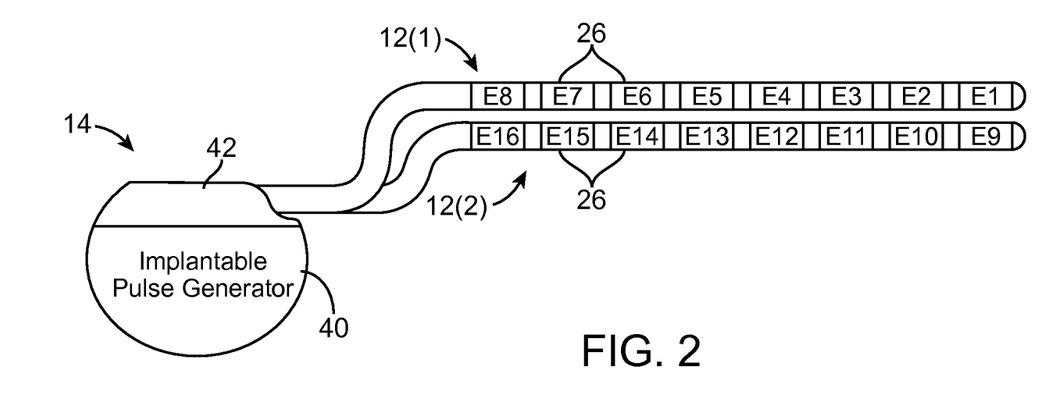
FIG. 2 is a plan view of an implantable pulse generator (IPG) and one embodiment of a stimulation lead used in the SCS system of FIG. 1.

Referring now to FIG. 2, the external features of the stimulation leads 12 and the IPG 14 will be briefly described. One of the stimulation leads 12 has eight electrodes 26 (labeled E1-E8), and the other stimulation lead 12 has eight electrodes 26 (labeled E9-E16). The actual number and shape of leads and electrodes will, of course, vary according to the intended application. The IPG 14 comprises an outer case 40 for housing the electronic and other components (described in further detail below), and a connector 42 to which the proximal ends of the stimulation leads 12 mate in a manner that electrically couples the electrodes 26 to the internal electronics (described in further detail below) within the outer case 40. The outer case 40 is composed of an electrically conductive, biocompatible material, such as titanium, and forms a hermetically sealed compartment wherein the internal electronics are protected from the body tissue and fluids. In some cases, the outer case 40 may serve as an electrode.

As briefly discussed above, the IPG 14 includes battery and pulse generation circuitry that delivers the electrical stimulation energy in the form of a pulsed electrical waveform to the electrode array 26 in accordance with a set of stimulation parameters programmed into the IPG 14. Such stimulation parameters may comprise electrode combinations, which define the electrodes that are activated as anodes (positive), cathodes (negative), and turned off (zero), percentage of stimulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), and pulse rate (measured in pulses per second), pulse shape, and burst rate (measured as the stimulation on duration per unit time).

Electrical stimulation will occur between two (or more) activated electrodes, one of which may be the IPG case 40. Simulation energy may be transmitted to the tissue in a monopolar or multipolar (e.g., bipolar, tripolar, etc.) fashion. Monopolar stimulation occurs when a selected one of the lead electrodes 26 is activated along with the case 40 of the IPG 14, so that stimulation energy is transmitted between the selected electrode 26 and case 40. Bipolar stimulation occurs when two of the lead electrodes 26 are activated as anode and cathode, so that stimulation energy is transmitted between the selected electrodes 26. For example, electrode E3 on the first lead 12 may be activated as an anode at the same time that electrode E11 on the second lead 12 is activated as a cathode. Tripolar stimulation occurs when three of the lead electrodes 26 are activated, two as anodes and the remaining one as a cathode, or two as cathodes and the remaining one as an anode. For example, electrodes E4 and E5 on the first lead 12 may be activated as anodes at the same time that electrode E12 on the second lead 12 is activated as a cathode.

The stimulation energy may be delivered between electrodes as monophasic electrical energy or multiphasic electrical energy. Monophasic electrical energy includes a series of pulses that are either all positive (anodic) or all negative (cathodic). Multiphasic electrical energy includes a series of pulses that alternate between positive and negative. For example, multiphasic electrical energy may include a series of biphasic pulses, with each biphasic pulse including a cathodic (negative) stimulation pulse and an anodic (positive) recharge pulse that is generated after the stimulation pulse to prevent direct current charge transfer through the tissue, thereby avoiding electrode degradation and cell trauma. That is, charge is conveyed through the electrode-tissue interface via current at an electrode during a stimulation period (the length of the stimulation pulse), and then pulled back off the electrode-tissue interface via an oppositely polarized current at the same electrode during a recharge period (the length of the recharge pulse).

The IPG 14 also comprises circuitry configured for delivering electrical energy to the electrode array 26 in a manner that blocks action potentials that propagate along sensory and motor neural fibers of the spinal cord in response to a high frequency continuous sinusoidal blocking signal. Further details discussing the modulating/blocking electrical energy will be discussed below.

Figure 3:
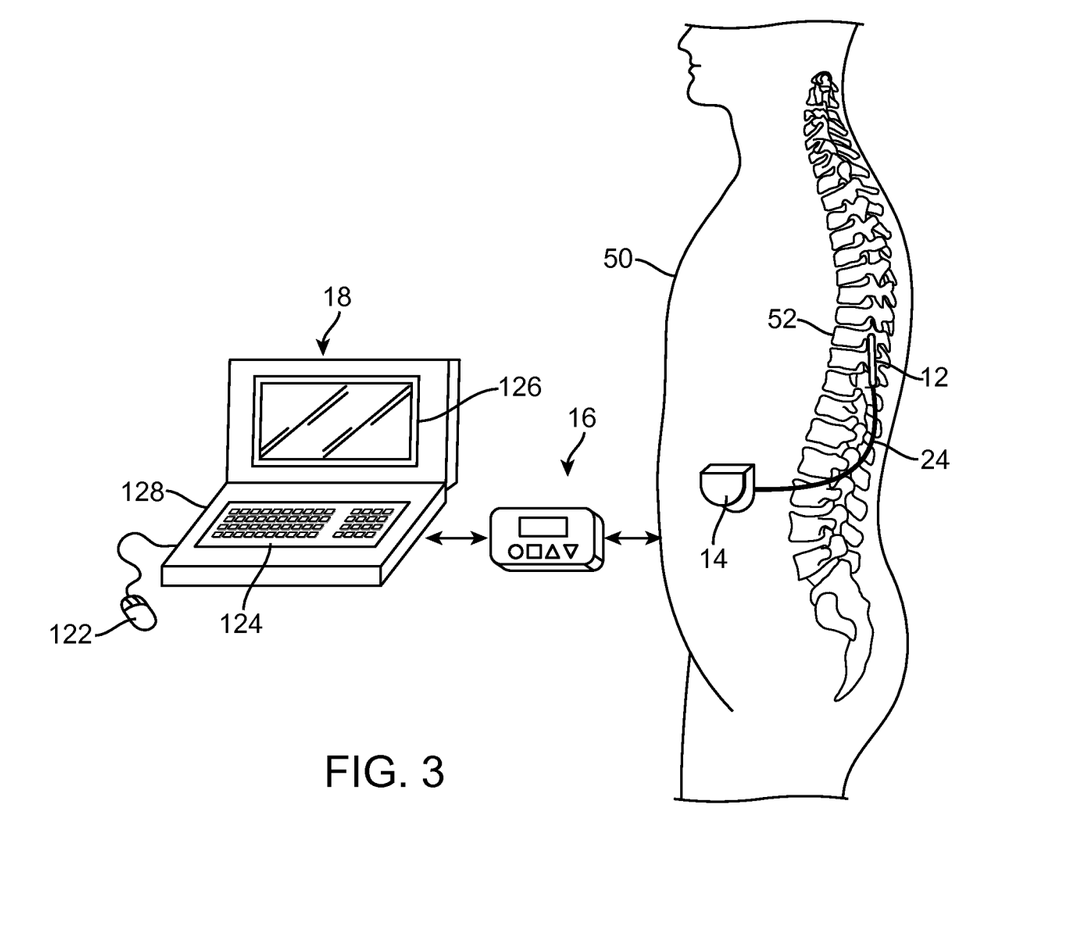
FIG. 3 is a plan view of the SCS system of FIG. 1 in use with a patient.

As shown in FIG. 3, the neurostimulation leads 12 are implanted within the spinal column 52 of a patient 50. The preferred placement of the neurostimulation leads 12 is adjacent, i.e., resting near, or upon the dura, adjacent to the spinal cord area to be stimulated. Due to the lack of space near the location where the neurostimulation leads 12 exit the spinal column 52, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neurostimulation leads 12. As there shown, the CP 18 communicates with the IPG 14 via the RC 16.

Figure 4:
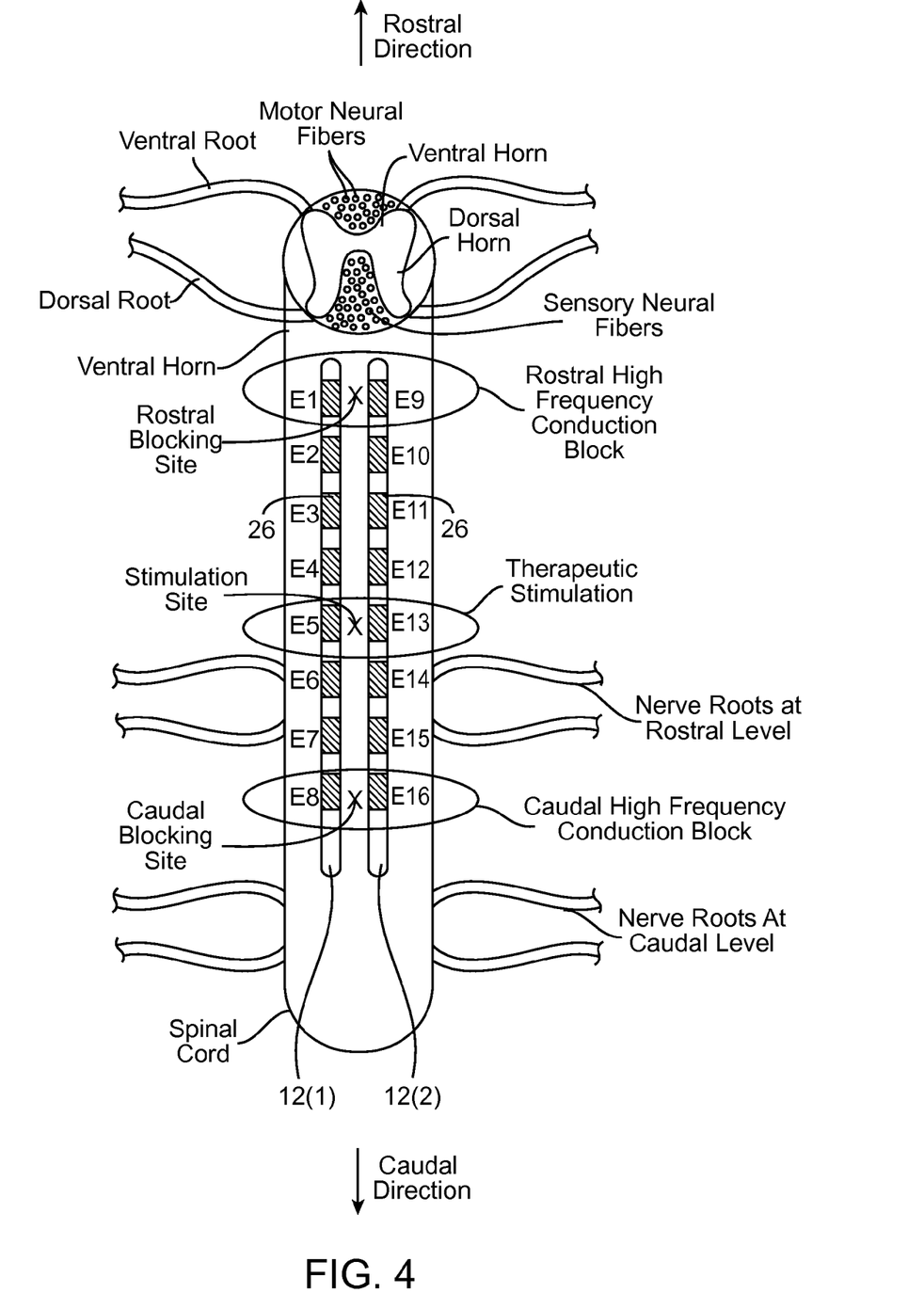
FIG. 4 is a plan view of neurostimulation leads of the SCS system used to stimulate a spinal cord to provide pain therapy to a patient, while rostrally and caudally blocking evoked action potential to prevent side-effects.

Referring now to FIG. 4, a method of using the SCS system 10 to treat a tissue region of a patient while reducing the sensation of paresthesia associated with that tissue region from being sensed by the patient and preventing other side-effects, such as involuntary movement of other tissue regions of the patient. As there shown, the two neurostimulation leads 12 are rostro-caudally placed along the spinal cord of the patient.

In this example, electrodes E5 and E13, which are located over a desired stimulation site, are configured as stimulating electrodes, with electrode combinations intended to stimulate the spinal cord tissue immediately adjacent to electrodes E5 and E13. A monopolar arrangement or other types of multi-polar arrangements can be made from the electrodes. The resulting pulsed electrical waveform conveyed between electrodes E5 and/or E13 and the stimulation site evokes action potentials (APs) that both orthodromically propagate (in this case, in the rostral direction) and antidromically propagate (in this case, in the caudal direction) along spinal cord sensory neural fibers, some of which are target neural fibers (i.e., sensory neural fibers that innervate the tissue region of the patient to be treated) that terminate in the dorsal horn of the spinal cord at a relatively rostral vertebral level, and others of which are non-target sensory neural fibers (i.e., sensory neural fibers that innervate the tissue region of the patient not be treated that facilitate spinal cord motor reflex loops) that terminate in dorsal horn of the spinal cord at a relatively caudal vertebral level.

As discussed above in the background of the invention, it is believed that the antidromic propagation of action potentials in the target sensory spinal cord neural fibers reduces/blocks transmission of smaller diameter sensory neural pain fibers via interneuronal interaction in the dorsal horn of the spinal cord, thereby creating the therapeutic effect of pain relief in the pain region, while the orthodromic propagation of action potentials in target sensory spinal cord neural fibers, if undisturbed, will arrive at the dorsal column nuclei, then the thalamus, and are relayed to the sensory cortex to create the paresthesia sensation corresponding to the pain region. The antidromic propagation of action potentials in the non-target motor-linked spinal cord neural fibers, if undisturbed, will be communicated to the ventral nerve roots via the ventral horn of the spinal cord that may create a side-effect in the form of involuntary motor movement of a tissue region, such as an arm or leg.

Electrodes E1 and E9, which are rostrally located relative to electrodes E5 and E13 over a rostral blocking site, are configured as blocking electrodes in a bipolar arrangement. Of course, other blocking electrode configurations, including a monopolar arrangement or other types of multipolar arrangements, can be made from the electrodes. In a preferred embodiment, the electrodes E1 and E9 generate a continuous blocking signal (which may be, e.g., sinusoidal) that has a high frequency relative to the pulse rate of the stimulation pulsed waveform generated by electrodes E5 and E13. In the illustrated embodiment, the pulse rate of the stimulation pulsed waveform is within a range of 2 Hz-1200 Hz, while the frequency of the blocking signal is greater than 1200 Hz, and preferably equal to or greater than 2000 Hz.

The resulting blocking signal conveyed between electrodes E1 and E9 and the rostral blocking site at the least attenuates, and preferably blocks, the orthodromically propagated action potentials conveyed along the target sensory spinal cord neural fibers at the blocking site, thereby reducing, and preferably eliminating, the paresthesia accompanying the therapeutic effect of pain relief that would have otherwise been sensed by the patient in the absence of the blocking signal. The blocking electrodes E1 and E9 are preferably far enough away from the stimulating electrodes E5 and E13, such that the electrical field created from the conveyance of the blocking signal does not affect, or minimally effects, the electrical field created by the conveyance of the pulsed electrical waveform by electrodes E5 and E13 at the stimulation site.

Electrodes E8 and E16, which are caudally located relative to electrodes E5 and E13 over a caudal blocking site, are configured as blocking electrodes in a bipolar arrangement. Of course, other blocking electrode configurations, including a monopolar arrangement or other types of multipolar arrangements, can be made from the electrodes. Like electrodes E1 and E9, electrodes E8 and E16 generate a continuous blocking signal that has a high frequency relative to the pulse rate of the stimulation pulsed waveform generated by electrodes E5 and E13. In the illustrated embodiment, the pulse rate of the stimulation pulsed waveform is within a range of 2 Hz-1200 Hz, while the frequency of the blocking signal is greater than 1200 Hz, and preferably equal to or greater than 2000 Hz.

The resulting blocking signal conveyed between electrodes E8 and E16 and the blocking site at the least attenuates, and preferably blocks, the antidromically propagated action potentials conveyed along the non-target motor-linked spinal cord sensory neural fibers at the caudal blocking site, thereby reducing, and preferably eliminating, any side-effects in the form of motor movement experienced by the patient in the absence of the blocking signal. The blocking electrodes E8 and E16 are preferably far enough away from the stimulating electrodes E5 and E13, such that the electrical field created from the conveyance of the blocking signal does not affect, or minimally effects, the electrical field created by the conveyance of the pulsed electrical waveform by electrodes E5 and E13 at the stimulation site. Preferably, the caudal blocking site at which the blocking signal is conveyed is located between the vertebral level at which the target sensory spinal cord neural fibers terminate in the dorsal horn and the vertebral level at which the non-target motor-linked sensory spinal cord neural fibers terminate in the dorsal horn, so that the blocking signal does not diminish the therapeutic effect created by the action potentials antidromically propagated along the target sensory neural fibers, and diminishes the side-effect created by the action potentials antidromically propagated along the motor-linked sensory neural fibers.

Further details describing the use of high frequency electrical energy to block the propagation of action potentials are set forth in U.S. Pat. No. 12/618,563, entitled "System and Method for Modulating Action Potential Propagation During Spinal Cord Stimulation," which is expressly incorporated herein by reference.

During a typical procedure, the neurostimulation leads 12 are implanted within the patient and either connected to the ETS 20 (in the case of a trial) or the IPG 14 (in the case of post-trial procedure) in the manner described with respect to FIG. 3, while ensuring that there are electrodes 26 well above and well below the electrodes 26 that will be used to provide the stimulation. Next, the stimulation parameters are adjusted in a conventional manner, such that the electrical field of the electrical pulsed waveform conveyed by the electrodes 26 is focused over the stimulation site in a manner that places the paresthesia concordant with the pain region of the patient. Following paresthesia concordance with the pain region, the blocking signals can be conveyed from the selected electrodes at the rostral and caudal blocking sites to minimize or eliminate the paresthesia and to prevent motor activation of other tissue regions of the patient. The amplitude of the electrical pulsed waveform can then be increased to optimize the therapy provided to the pain region without concern that the paresthesia will increase to an uncomfortable level and/or involuntary movement of other tissue regions of the patient will occur.

Although the foregoing method as been described as simultaneously providing a rostral blocking signal to minimize paresthesia in the patient and a caudal blocking signal to minimize motor movement in the patient, it should be appreciated that the rostral and caudal blocking signals can be independently provided to the patient.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a tissue region of a patient using first and second electrodes, comprising:
   conveying an electrical pulsed waveform between the first electrode and a stimulation site of a spinal cord of the patient, thereby evoking the antidromic propagation of action potentials along at least one sensory neural fiber of the spinal cord that creates a therapeutic effect in the tissue region, and evoking the orthodromic propagation of action potentials along the at least one sensory neural fiber that potentially creates a sensation of paresthesia in the brain of the patient corresponding to the tissue region; and
   conveying electrical energy between the second electrode and a blocking site of the spinal cord rostral to the stimulation site, thereby blocking the orthodromically propagated action potentials and reducing the paresthesia that would have otherwise been caused in the patient in the absence of the conveyed electrical energy.

2. The method of claim 1, wherein the electrical pulsed waveform between the first electrode and the stimulation site evokes the antidromic propagation of action potentials along at least another sensory neural fiber of the spinal cord that potentially creates a side-effect in another tissue region of the patient, the method further comprising conveying additional electrical energy between a third electrode and a blocking site of the spinal cord caudal to the stimulation site, thereby blocking the action potentials propagated along the at least other sensory neural fiber and reducing the side-effect that would have otherwise been caused in the patient in the absence of the additionally conveyed electrical energy.

3. The method of claim 2, wherein the side-effect is involuntary motor movement of the other tissue region.

4. The method of claim 1, wherein the action potentials antidromically propagated along the at least one sensory neuron reduce, via interneuronal interaction in a dorsal horn of the patient, antidromic propagation of action potentials in sensory neural fibers in the spinal cord innervating the tissue region.

5. The method of claim 1, wherein the therapeutic effect is pain relief.

6. The method of claim 1, wherein the electrical energy is sinusoidal.

7. The method of claim 6, wherein the sinusoidal energy has a frequency greater than a pulse rate of the electrical pulsed waveform.

8. The method of claim 7, wherein the pulse rate of the electrical pulsed waveform is within a range of 2 Hz-1200 Hz, and the frequency of the sinusoidal energy is greater than 1200 Hz.

9. The method of claim 8, wherein the frequency of the electrical energy is equal to or greater than 2000 Hz.

10. The method of claim 1, wherein the at least one sensory neural fiber is a plurality of sensory neural fibers.

11. The method of claim 1, wherein the blocking of the orthodromically propagated potentials eliminates the paresthesia that would have otherwise been caused in the patient in the absence of the conveyed electrical energy.

12. A method of providing therapy to a tissue region of a patient using first and second electrodes, comprising:
    conveying an electrical pulsed waveform between the first electrode and a stimulation site of a spinal cord of the patient, thereby evoking the antidromic propagation of action potentials along at least a first sensory neural fiber of the spinal cord that creates a therapeutic effect in the tissue region, and evoking the antidromic propagation of action potentials along at least another sensory neural fiber of the spinal cord that potentially creates a side-effect in another tissue region, wherein the at least first sensory neural fiber terminates in a dorsal horn of the spinal cord at a first vertebral level, and the at least second sensory neural fiber terminates in the dorsal horn at a second vertebral level caudal to the first vertebral level; and
    conveying electrical energy between the second electrode and a blocking site of the spinal cord between the first and second vertebral levels, thereby blocking the action potentials antidromically propagating along the at least second sensory neural fiber and reducing the side-effect that would have otherwise been caused in the patient in the absence of the conveyed electrical energy.

13. The method of claim 12, wherein the electrical pulsed waveform between the first electrode and the stimulation site evokes the orthodromic propagation of action potentials along the at least one sensory neural fiber that potentially creates a sensation of paresthesia in the brain of the patient corresponding to the tissue region, the method further comprising conveying additional electrical energy between a third electrode and a blocking site of the spinal cord rostral to the stimulation site, thereby blocking the orthodromically propagated action potentials and reducing the paresthesia that would have otherwise been caused in the patient in the absence of the conveyed electrical energy.

14. The method of claim 12, wherein the side-effect is involuntary motor movement of the other tissue region.

15. The method of claim 12, wherein the action potentials antidromically propagated along the at least one sensory neural fiber reduce, via interneuronal interaction in the dorsal horn of the patient, antidromic propagation of action potentials in sensory neural fibers in the spinal cord innervating the tissue region.

16. The method of claim 12, wherein the therapeutic effect is pain relief.

17. The method of claim 12, wherein the electrical energy is sinusoidal.

18. The method of claim 17, wherein the sinusoidal energy has a frequency greater than a pulse rate of the electrical pulsed waveform.

19. The method of claim 18, wherein the pulse rate of the electrical pulsed waveform is within a range of 2 Hz-1200 Hz, and the frequency of the sinusoidal energy is greater than 1200 Hz.

20. The method of claim 19, wherein the frequency of the electrical energy is equal to or greater than 2000 Hz.

21. The method of claim 12, wherein the at least one sensory fiber is a plurality of sensory neural fiber.

22. The method of claim 12, wherein the blocking of the action potentials antidromically propagated along the at least second sensory neural fiber eliminates the side-effect that would have otherwise been caused in the patient in the absence of the conveyed electrical energy.

* * * * *